United States Patent [19]

Beauchemin, Jr.

[11] 4,080,834
[45] Mar. 28, 1978

[54] MEASUREMENT OF FUEL QUALITY AND ECONOMY

[76] Inventor: George A. Beauchemin, Jr., 14 Royal Cr. Dr., No. 12, Nashua, N.H. 03060

[21] Appl. No.: 690,431

[22] Filed: May 27, 1976

Related U.S. Application Data

[63] Continuation-in-part of Ser. No. 581,870, May 29, 1975, abandoned.

[51] Int. Cl.² .......................................... G01M 19/00
[52] U.S. Cl. ..................................................... 73/443
[58] Field of Search ................. 73/233, 113, 443, 442, 73/190 CV

[56] References Cited

U.S. PATENT DOCUMENTS

| | | | |
|---|---|---|---|
| 2,668,440 | 2/1954 | Wilson | 73/443 |
| 3,224,273 | 12/1965 | Granberg | 73/233 |

Primary Examiner—Jerry W. Myracle
Attorney, Agent, or Firm—S. Z. Szczepanski

[57] ABSTRACT

A device and a process for measuring fuel quality and/or economy is provided by this invention. The specific gravity of fuel is measured by any suitable means such as a hydrometer; the temperature of fuel is measured by another means, such as, a thermometer. Third means responsive to the measurements obtained by first two means converts the specific density of the fuel to specific density at a predetermined temperature and from that to fuel quality. The fuel quality can then be converted to fuel economy when the price of fuel is known. Alternatively, specific density of fuel corrected to the specific density at a predetermined temperature can be converted directly to fuel economy if the price of the fuel is known. For conversions described above suitable nomographs can be used.

12 Claims, 3 Drawing Figures

MEASUREMENT OF FUEL QUALITY AND ECONOMY

This invention is a continuation-in-part of a copending application Ser. No. 581,870 filed May 29, 1975, now abandoned.

FIELD OF INVENTION

The present invention relates to fuel economy and/or quality measuring devices and to methods of determining fuel quality and/or economy. In particular it relates to fuel quality and/or economy measuring devices which are based on determination of fuel specific gravity at a selected standard temperature.

BACKGROUND OF THE INVENTION

Traditionally gasoline fuel economy is thought of in terms of miles per gallon. Since driving conditions vary considerably, it is quite difficult for a driver to accurately measure fuel economy in order to decide which fuel yields the most miles per dollar. One can assume, that gasoline has the proper additives to be substantially completely combustible. With this assumption it is possible to measure the caloric value of gasoline and to thereby determine which gasoline is the most economical. It is known that for fuels such as oil the caloric value is a function only of specific gravity corrected to a standard temperature. With my assumption of complete combustability, I believe this relationship is also applicable to gasoline. The mathematical relationships for determining fuel economy from the quantities of specific gravity, temperature and fuel cost per gallon are however too unwieldly and time consuming for the average person.

The present invention obviates some of the problems presented by the prior art.

It is therefore one object of the invention to provide an apparatus and a method for measuring fuel quality and for economy by testing a small sample of the fuel.

Another object of the invention is to provide for efficient, inexpensive and accurate measurement of fuel quality and/or economy.

Further object of the invention is to provide for measurement of quality and/or fuel economy using a minimum number of operations.

Still further object of the invention is to provide for measurement of fuel quality and/or economy which is independent of driving conditions.

Still another object of the invention is to provide for measurement of fuel economy which can be accomplished regardless of whether the vehicle is moving or is stationary.

Other objects of this invention will become apparent to those skilled in the art upon studying this disclosure.

SUMMARY OF THE INVENTION

In accordance with one aspect of the invention fuel specific density is measured by a suitable means such as a hydrometer. Fuel temperature is measured by suitable means such as a thermometer. The measured fuel specific density is then corrected to fuel specific density at a preselected temperature using another means such as a nomograph. Utilizing a correlation between fuel specific density at a preselected temperature and fuel caloric value, fuel caloric value is obtained by means of another nomograph or other suitable means.

In accordance with another aspect of the invention fuel caloric value is converted to the caloric value per dollar by any suitable means including a nomograph.

In accordance with a further aspect of the invention there is provided a transparent container holding stacked weights of varying densities to form a hydrometer and a thermometer capillary. A squeeze bulb is provided for drawing fluid into the transparent container via a hose connected to a bottom end of the container. To first correct the measured specific gravity to standard temperature, a nomograph link is provided straddling the weight stack and the thermometer and rides in tracks of disengagable friction members. By momentarily disengaging the friction members, the link may be lined up both with the top most non-floating weight and the surface of fluid in the thermometer. As a result a pivot point carried by the link assumes a position indicative of specific gravity corrected to standard temperature. A second link mounted on the pivot, is rotated to be in line with a reading on a fuel cost scale. The intersection of the second link, so positioned, with a caloric value per dollar scale indicates the economy of the fuel.

Other aspects, features and advantages of the present invention will become apparent upon perusal of the specifications and claims appended thereto.

DETAILED DESCRIPTION

Figure 1:
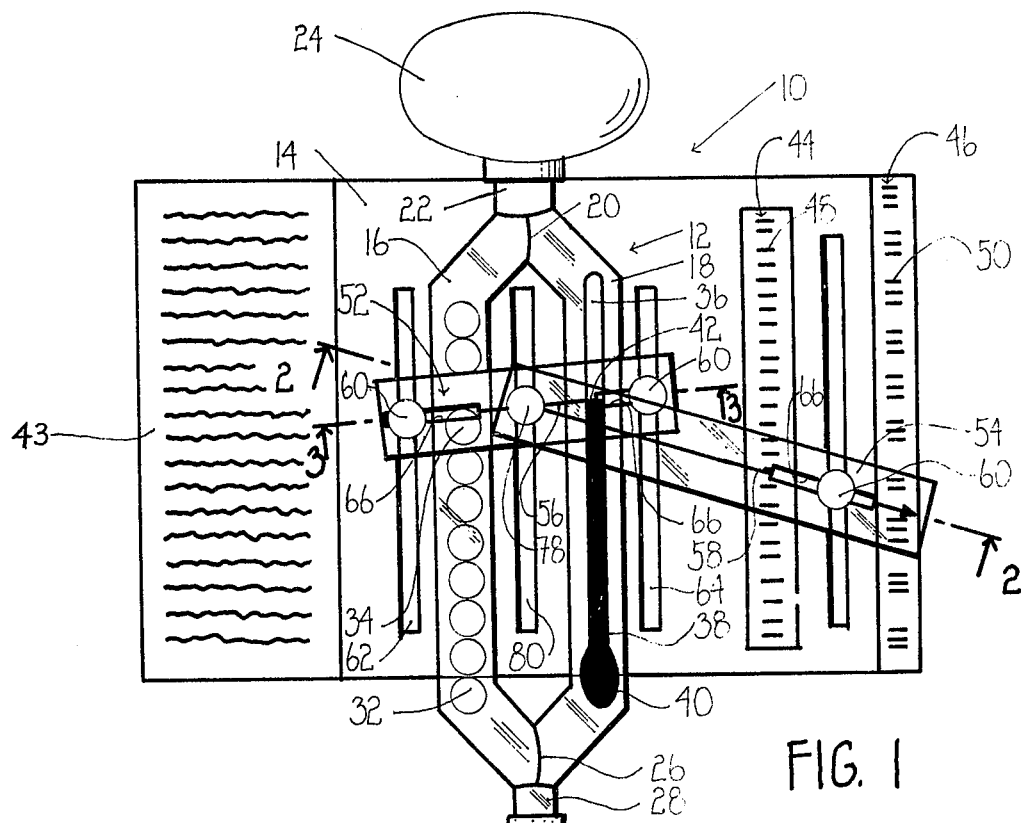
FIG. 1 is a front elevation view of the fuel economy measuring device of the present invention.

Referring to FIG. 1, the fuel economy measuring device 10 of the present invention comprises an elongated transparent container 12 mounted on a rectangular plate 14, as of plastic, which is adapted to be held vertically. The container 12 comprises a pair of spaced apart vertical tubular branches 16 and 18 which are merged at their top ends in a "Y" junction 20 having a tubular part 22 which is capped by a squeeze bulb 24. The branches 16 and 18 are also merged at their bottoms to another "Y" junction 26 having a tubular port 28 on which is fitted a length of flexible hose 30, as of rubber. By placing the free end of hose 30 into a reservoir for fuel, and squeezing bulb 24 sufficient fuel may be sucked into the branches 16 and 18 to fill the branches.

Branch 16 serves as a hydrometer for the fuel which is sucked into the branch. To provide a measure of specific gravity plural spherical plastic weights 32 of graduated densities are stacked vertically in the branch. The density of each weight 32 is less than the weight below. Thus the specific gravity of the fuel is indicated by the location of the topmost weight, such as 34, which is not carried upwards or floated in the fuel.

For measure the fuel temperature, the branch 18 contains a vertically oriented thermometer 36, of the type having a straight capillary 38 connected to a reservoir 40 for thermally expandable fluid. The position of the expandable fluid surface 42 in capillary 38 is thus indicative of the temperature of the fuel sucked into branch 18.

There is further provided on plate 14 one side of container 12, a strip region 43 for the printed instructions in the use of device 10. On the opposite side of container 12 are a pair of spaced apart vertically oriented scales 44 and 46. Scale 44, the closest to container 12, is graduated in markings giving units of cents per gallon. The other scale 46 is graduated in markings 50 indicative of fuel economy such as BTU per dollar.

Figure 3:
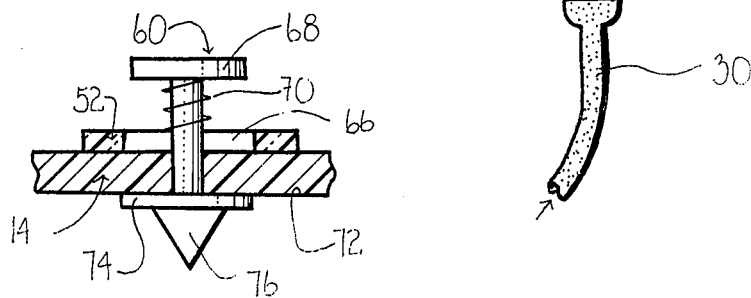
FIG. 3 is in partial cross-sectional view taken along the lines 3—3 in FIG. 1.
Figure 2:
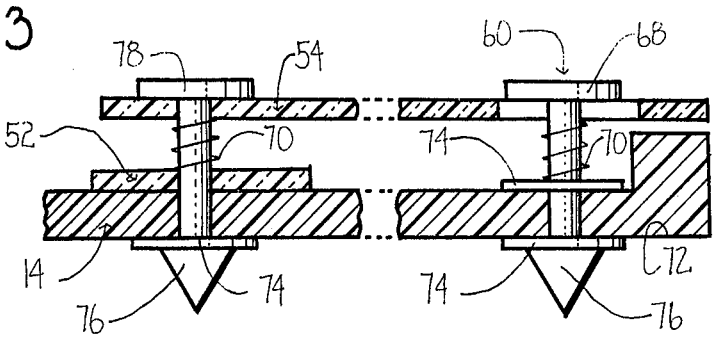
FIG. 2 is a cross-sectional view taken along the lines 2—2 in FIG. 1.

Referring also to FIGS. 2 and 3, a pair of transparent links 52 and 54, as of plastic, respectively carry control ruled lines 56 and 58 which form a nomograph for computing fuel economy from specific gravity, temperature and fuel cost. Link 52, which straddles branches 16 and 18 is supported at its opposite ends on two friction pins 60 which ride in a pair of vertically oriented slots 62 and 64 on opposite sides of container 12. To permit link 52 to be slid up and down and to be angulated so that line 56 may intersect both the topmost non-floating weight 34 and the surface 42 of fluid in capillary 38, the pins 60 are captured in central longitudinal slots 66.

Referring specifically to FIG. 3, each of the pins 60 comprise a nail 68 which passes through a compression spring 70, then through the slot 66 in the link 52 and then thru the slot 62 or 64 in the plastic plate 14. At the back side 72 of plate 14, nail 68 receives a washer 74, having a roughened surface, and a snap on cap 76. Due to the roughened surface on washer 74, which is pressed against back surface 72, by the action of spring 70, the link 52 is maintained in position along the slots 62 and 64. To move the link 52, the heads of nails 68 are pushed to disengage washers 74 from back surface 72.

To provide a positional indication of specific gravity corrected to a standard temperature, the densities of weights 32 are graduated in a manner for the position of pivot pin 78 for link 54, along a vertically oriented slot 80 between branches 16 and 18 in which pin 78 rides to satisfy the following equation for correction of specific gravity for thermal expansion of the volume of the fuel:

$$s = S_T/[1 + 0.00044 (T - 60)]$$

where:
 $S$ = specific gravity at a standard temperature of 60° F;
 $S_T$ = specific gravity measured in branch 16; and
 $T$ = temperature measured in branch 18 in degrees Fahrenheit.

Pin 78 passes first through link 54, then through a spring 70, then through link 52 and then through plate 14 to obviate any motion of the links perpendicular to slot 80.

There is further provided a vertically oriented slot in plate 14 between the scales 44 and 46 in which another friction pin 60 rides after passing through a longitudinal slot 66 in link 54 to enable the link to rotate about pivot pin 78. Since link 54 stands out from plate 14 a greater distance then link 52, the spring 70 is threaded onto nail 68 between link 66 and plate 14 for spacing the link for the plate. The link 54 is rotated about pin 78 by momentarily pushing pin 68, as in the case with link 52, to momentarily disengage the washer 74 from back surface 72. The link is then rotated with line 58 intersecting the desired numeral on fuel cost scale 44 indicative of the cost per gallon on the fuel under test. The intersection of line 58 with the fuel economy scale 46 is then noted.

The scales 44 and 46 are graduated in a manner to satisfy an equation of the form:

$$B = [K_1 S (K_2 - S^2)]/F$$

where:

$B$ = the indication on the fuel economy scale in terms of caloric value per dollar;
 $S$ = specific gravity corrected to standard temperature;
 $K_1$ = a constant scale factor;
 $K_2$ = an empirical constant; and
 $F$ = fuel cost in cents per gallon.

Having described the preferred embodiment of the fuel economy measuring device of the present invention, in great detail it should be apparent that numerous modifications, additions and omissions in the details thereof are possible within the spirit and scope of the invention.

For example, although the measurement of specific density described in the specific embodiment involved determining which of the weights immersed in the fuel was most nonfloating any other means of determining specific gravity which can give a reading on a scale is suitable for the use in connection with this invention either using a float or otherwise. Similarly, although the temperature of the fuel was measured by means of a capillary tube having expandable fluid therein any other means of measuring the temperature of the fuel which can give a reading on a scale is appropriate for the use with this invention. To convert the reading movable links were used to form nomographs; it should be emphasized however that any other method for converting measurements of fuel specific gravity and its temperature to fuel caloric value and fuels caloric value per dollar are acceptable for the use with this invention.

It should also be emphasized that when nomographs are used for conversions the positions of individual scales and indicators with respect to each other and one another are such as to satisfy equations forming nomographs. Thus, the scale on the means which indicates specific gravity of fuel and the indicator of the thermometer should be in such locations with respect to each other as to allow formation of the first nomograph for converting the specific gravity of the fuel measured by the hydrometer and temperature measured by the thermometer to a specific gravity of fuel at a standard predetermined temperature. Similarly, the other scales must be adapted to form required nomographs.

Many other modifications will become apparent to those skilled in the art upon studing this disclosure. All such modifications which fall within the spirit of this invention are intended to be included within its scope.

I claim:

1. A device for determining the economy of a fuel comprising:
 first means for obtaining a reading of specific gravity of the fuel;
 second means for obtaining a reading of temperature of the fuel;
 a price of the fuel scale;
 a caloric value per dollar scale; and
 nomograph means for converting the reading of the specific gravity of the fuel appearing on said first means, the reading of temperature of the fuel appearing on said second means and price of the fuel on said price scale to caloric value per dollar on said caloric value per dollar scale.

2. A device as claimed in claim 1 further comprising a corrected specific gravity scale;
 wherein:
 said nomograph means comprises:
 a first link extending across said first and second means and to said corrected specific gravity scale; said corrected specific gravity scale being in such a location with respect to readings of said first and second means as to allow the formation of a first nomograph satisfying the equation expressing specific gravity corrected to a predetermined temperature as a function of measured specific gravity and the temperature of said fuel; and, a second link extending from said corrected specific gravity scale across said price of the fuel scale to said caloric value per dollar scale, said caloric value per dollar scale being in such location as to allow formation of a second nomograph satisfying the equation expressing caloric value of fuel per dollar as a function of specific gravity of the fuel corrected to a predetermined temperature and the price of the fuel.

3. A device as claimed in claim 2 wherein:
said first means comprises a hydrometer;
said second means comprises a capillary-type thermometer;
the first nomograph satisfies the equation:

$$S = S_T/[1 + 0.00044 (T-60)]$$

where:
$S$ = specific gravity of the fuel at a standard temperature of 60° F,
$S_T$ = specific gravity of the fuel,
$T$ = temperature of the fuel; and
the second nomograph satisfies the equation:

$$B = [K_1 S (K_2 - S^2)]/F$$

where:
$B$ = caloric value per dollar of fuel,
$K_1$ = a constant scale factor,
$K_2$ = an empirical constant,
$F$ = price of the fuel,
$S$ = specific gravity of the fuel at a standard temperature of 60° F.

4. A device for determining the economy of a fuel comprising:
first means for obtaining a reading of specific gravity of the fuel;
second means for obtaining a reading of temperature of the fuel;
a price of the fuel scale;
a fuel caloric value per dollar scale;
first aligning means for forming a first nomograph by aligning readings of said first and said second means to obtain a reading of specific gravity of the fuel, corrected to a predetermined temperature;
second aligning means for forming a second nomograph by aligning the reading of the corrected specific gravity of the fuel with the price of the fuel on the price of the fuel scale to obtain fuel caloric value per dollar on said fuel caloric value per dollar scale, the readings of said first and second means, the price scale and the fuel caloric value per dollar scale being so arranged with respect to one another as to allow the formation of said nomographs satisfying an equation expressing the corrected density as a function of temperature and measured specific gravity, and the equation expressing caloric value of fuel per dollar as a function of temperature and corrected specific gravity of said fuel, respectively.

5. A device as claimed in claim 4 wherein:
said first means comprises a hydrometer; and
said second means comprises a thermometer.

6. A device as claimed in claim 4 wherein:
said first means comprises a vertically oriented hydrometer branch and a plurality of weights of graduated densities, stacked inside said hydrometer branch, the density of each weight being less than that of the weight below it.

7. A device as claimed in claim 6 wherein:
said second means comprises a vertically oriented thermometer branch and a capillary having thermally expandable fluid therein, said capillary being vertically oriented inside said thermometer branch.

8. A device as claimed in claim 7 wherein:
said first aligning means comprises a first link for aligning the top non-floating weight and the temperature reading to obtain the specific gravity corrected to standard temperature of 60° F, said first nomograph satisfying the following equation:

$$S = S_T[1 + 0.00044 (T-60)]$$

where:
$S$ = specific gravity of the fuel at a standard temperature of 60° F,
$S_T$ = measured specific gravity of the fuel,
$T$ = temperature of the fuel, and
a second link member for aligning the specific gravity of the fuel at a standard temperature of 60° F, obtained by the first aligning means with the price of the fuel to obtain fuel caloric value per dollar, said second nomograph satisfying the equation:

$$B = [K_1 S (K_2 - S^2)]/F$$

where:
$B$ = caloric value per dollar of fuel,
$K_1$ = a constant scale factor,
$K_2$ = an empirical constant,
$F$ = price of the fuel.

9. A device as claimed in claim 8 wherein said thermometer and said hydrometer branches communicate with each other, further comprising drawing means for drawing fuel into said thermometer and said hydrometer branches.

10. A device as claimed in claim 9 wherein said drawing means comprises a squeezing bulb.

11. A process for determining the fuel economy comprising the following steps:
(a) obtaining a temperature reading of the fuel on a temperature scale;
(b) obtaining a specific gravity of the fuel reading on a specific gravity scale;
(c) aligning temperature and specific gravity readings to form a first nomograph giving the specific gravity of the fuel corrected to a standard predetermined temperature on a corrected specific gravity scale;
(d) aligning the value of corrected specific gravity obtained in step "C" with the price of the fuel on a price scale to form a second nomograph giving the caloric value of fuel per dollar on a caloric value of fuel per dollar scale.

12. A process as claimed in claim 11 wherein: said first nomograph satisfies the equation:

$$S = S_T/[1 + 0.00044 (T-60)]$$

where:
- $S$ = specific gravity of the fuel at a standard temperature of 60° F,
- $S_T$ = specific gravity of the fuel,
- $T$ = temperature of the fuel; and said second nomograph satisfies the equation:

$$B = [K_1 S (K_2 - S^2)]/F$$

where:
- $B$ = caloric value per dollar of fuel,
- $K_1$ = a constant scale factor,
- $K_2$ = an empirical constant.

* * * * *